US009139860B2

(12) United States Patent
Chun

(10) Patent No.: US 9,139,860 B2
(45) Date of Patent: Sep. 22, 2015

(54) SIGNAL-AMPLIFYING FOLDED OLIGONUCLEOTIDE

(75) Inventor: Hong Gu Chun, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 398 days.

(21) Appl. No.: 13/084,148

(22) Filed: Apr. 11, 2011

(65) Prior Publication Data

US 2012/0259104 A1 Oct. 11, 2012

(51) Int. Cl.

| | |
|---|---|
| ***C07H 21/00*** | (2006.01) |
| ***C07H 21/04*** | (2006.01) |
| ***C12Q 1/00*** | (2006.01) |
| ***C12Q 1/68*** | (2006.01) |
| ***C12Q 1/70*** | (2006.01) |

(52) U.S. Cl.

CPC *C12Q 1/00* (2013.01); *C12Q 1/682* (2013.01); *C12Q 1/703* (2013.01)

(58) Field of Classification Search

None

See application file for complete search history.

(56) References Cited

U.S. PATENT DOCUMENTS

2005/0027461 A1* 2/2005 Shannon et al. ................ 702/20
2009/0106853 A1* 4/2009 Shekdar et al. ................ 800/21

* cited by examiner

*Primary Examiner* — Kenneth R. Horlick
*Assistant Examiner* — David Thomas
(74) *Attorney, Agent, or Firm* — Mintz Levin Cohn Ferris Glovsky and Popeo, P.C.; Kongsik Kim; Elaine Morlock

(57) ABSTRACT

The present invention relates to a self-amplifying folded oligonucleotide structure for sensitive oligonucleotide sensing without polymerase chain reaction (PCR). A self-amplifying folded oligonucleotide structure comprise a target sensing sequence having stem loop structure, a signaling molecule and signal modifying molecule labeled two stems wherein the two stems include oligonucleotide sequence that is complementary to a target sensing sequence of another self-amplifying folded oligonucleotide structure.

11 Claims, 4 Drawing Sheets

SEQUENCE LISTING

<160> NUMBER OF SEQ ID NOS: 7

<210> SEQ ID NO 1
<211> LENGTH: 51
<212> TYPE: DNA
<213> ORGANISM: Artificial Sequence
<220> FEATURE:
<223> OTHER INFORMATION: A signal-amplifying oligonucleotide

<400> SEQUENCE: 1
gcggaagggg gaagccgctc catttagtac tgtccggcaa cccccaaccg c 51

<210> SEQ ID NO 2
<211> LENGTH: 17
<212> TYPE: DNA
<213> ORGANISM: Human immunodeficiency virus

<400> SEQUENCE: 2
gacagtacta aatggag 17

<210> SEQ ID NO 3
<211> LENGTH: 28
<212> TYPE: DNA
<213> ORGANISM: Artificial Sequence
<220> FEATURE:
<223> OTHER INFORMATION: 5' portion of a signal-amplifying oligonucleotide after cleavage

<400> SEQUENCE: 3
gcggaagggg gaagccgctc catttagt 28

<210> SEQ ID NO 4
<211> LENGTH: 23
<212> TYPE: DNA
<213> ORGANISM: Artificial Sequence
<220> FEATURE:
<223> OTHER INFORMATION: 3' portion of a signal-amplifying oligonucleotide after cleavage

<400> SEQUENCE: 4
actgtccggc aacccccaac cgc 23

<210> SEQ ID NO 5
<211> LENGTH: 17
<212> TYPE: DNA
<213> ORGANISM: Artificial Sequence
<220> FEATURE:
<223> OTHER INFORMATION: A target sensing sequence of a signal-amplifying oligonucleotide

<400> SEQUENCE: 5
ctccatttag tactgtc 17

<210> SEQ ID NO 6
<211> LENGTH: 17
<212> TYPE: DNA
<213> ORGANISM: Artificial Sequence
<220> FEATURE:
<223> OTHER INFORMATION: A first region of a signal-amplifying oligonucleotide -continued

```
<400> SEQUENCE: 6

cggcaacccc caaccgc                                                    17


<210> SEQ ID NO 7
<211> LENGTH: 17
<212> TYPE: DNA
<213> ORGANISM: Artificial Sequence
<220> FEATURE:
<223> OTHER INFORMATION: A second region of a signal-amplifying
      oligonucleotide

<400> SEQUENCE: 7

gcggaagggg gaagccg                                                    17
```

SIGNAL-AMPLIFYING FOLDED OLIGONUCLEOTIDE

CLAIM FOR PRIORITY

This application claims priority to Provisional Applications No. 61/341,904 filed on Apr. 7, 2010 in the USPTO, the entire contents of which is hereby incorporated by reference.

SEQUENCE LISTING

The instant application contains a Sequence Listing which has been submitted in ASCII format via EFS-Web and is hereby incorporated by reference in its entirety. Said ASCII copy, created on Aug. 29, 2013, is named 88486-50498-ST25.txt and is 1,800 bytes in size.

BACKGROUND

1. Technical Field

The present invention relates to a self-amplifying folded oligonucleotide structure for sensitive oligonucleotide sensing.

2. Related Art

The present invention relates to diagnostics. More particularly, the present invention relates to diagnostics based on DNA, RNA or PNA sensing.

The specific application includes HIV diagnosis. Early and accurate HIV diagnosis for infants in developing countries is a serious challenge for AIDS management. Enzyme-linked immunosorbent assay (ELISA) is the most common method for point of care HIV diagnosis, but it cannot distinguish between maternal and infant antibodies. Therefore, we need highly sensitive nucleic acid based assays such as real-time PCR and NASBA. But, the real-time PCR and NASBA are not applicable in resource limited settings.

SUMMARY

The present invention relates to a self-amplifying folded oligonucleotide structure for sensitive oligonucleotide sensing. In one embodiment of the invention, there is provided a self-amplifying folded oligonucleotide structure comprising a target sensing sequence having stem loop structure, a signaling molecule and signal modifying molecule labeled two stems wherein the two stems oligonucleotide sequence that is complementary to a target sensing sequence of another self-amplifying folded oligonucleotide structure. Preferably, one of the two stems is labeled with a signaling molecule and the other one is labeled with a signal modifying molecule.

In another embodiment, said the target sensing sequence may include an oligonucleotide sequence capable of binding to a stem of another self-amplifying folded oligonucleotide structure or a target oligonucleotide sequence.

In yet another embodiment, said the target oligonucleotide sequence may include a DNA, RNA or PNA sequence. In a preferred embodiment, the DNA or RNA sequence may be a part of DNA or RNA sequences of HIV.

In one embodiment, said two stems are partially complementary to each other so that they can make a stem structure of the self-amplifying folded oligonucleotide when they hybridize.

In one embodiment, said target sensing sequence may have restriction site. The target oligonucleotide hybridized and unzipped structure may be mixed with cutting molecule, resulting in dividing of the target oligonucleotide hybridized and unzipped structure into two sub-molecules, namely unzipped-stem-one molecule and unzipped-stem-two molecule. Then, the divided unzipped-stem-one molecule and unzipped-stem-two molecule higher degree of freedom compared to the target oligonucleotide hybridized and unzipped structure, and therefore, results in efficient hybridization and unzipping reactions.

In one embodiment, said the signaling molecule and the signal modifying molecule are selected from a group of a fluorophore and fluorescence quencher, Raman label and surface-enhanced Raman scattering (SERS) inducing metal nanoparticle, or fluorescence resonance energy transfer (FRET) acceptor and donor.

Figure 1:
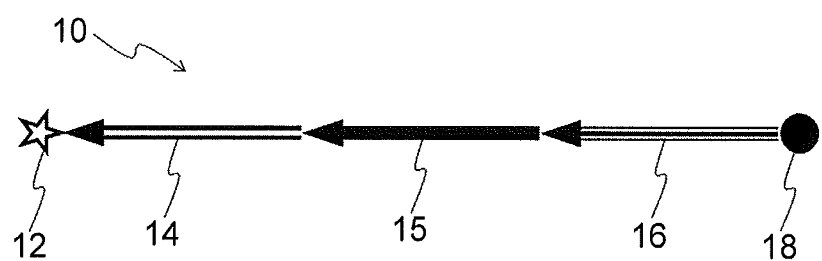
FIG. 1 is a linear structure of a self-amplifying folded oligonucleotide of the present invention.

12: signaling molecule
13: modified signaling molecule
14: stem-one oligonucleotide sequence
15: sensing oligonucleotide sequence
16: stem-two oligonucleotide sequence
18: signal modifying molecule
32: target DNA (or RNA or PNA) sequence
79: HIV 1 HXB2CG sequence (5'-GACAGTACTAAATGGAG-3'; SEQ ID NO.: 2)
85: cutting molecule
90: self-hybridized structure set
120: self-hybridized structure set

DESCRIPTION OF EXAMPLE EMBODIMENTS OF THE PRESENT INVENTION

Example embodiments of the present invention are disclosed herein. However, specific structural and functional details disclosed herein are merely representative for purposes of describing example embodiments of the present invention, however, example embodiments of the present invention may be embodied in many alternate forms and should not be construed as limited to example embodiments of the present invention set forth herein.

Accordingly, while the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention. Like numbers refer to like elements throughout the description of the figures.

Referring now to FIG. 1, there is shown a linear structure of a self-amplifying folded oligonucleotide 10 having a signaling molecule 12, signal modifying molecule 18, and a sensing oligonucleotide sequence 15 that is specific to a target DNA (or RNA or PNA), and two stem oligonucleotide sequences, namely a stem-one oligonucleotide sequence 14 and a stem-two oligonucleotide sequence 16. Arrow of each oligonucleotide sequence 14, 15 and 16 shows the direction of the DNA (or RNA or PNA). For example, in case of DNA, the arrow indicates 5' to 3' direction. The signaling molecule 12 and signal modifying molecule 18 are attached to each end of the self-amplifying folded DNA (or RNA or PNA).

In more detail, still referring to FIG. 1, the signaling molecule 12 shows different signaling characteristic when it is near the signal modifying molecule 18. Examples for the signaling molecule 12 and the signal modifying molecule 18 pair include fluorophore and fluorescence quencher, Raman label and surface-enhanced Raman scattering (SERS) inducing metal nanoparticle, and fluorescence resonance energy transfer (FRET) acceptor and donor, respectively. The sensing oligonucleotide sequence 15 can hybridize to a target oligonucleotide sequence. The stem-one oligonucleotide sequence 14 and stem-two oligonucleotide sequence 16 are partially complement to each other so that they can make a stem structure of the a self-amplifying folded oligonucleotide when they hybridize.

Figure 2:
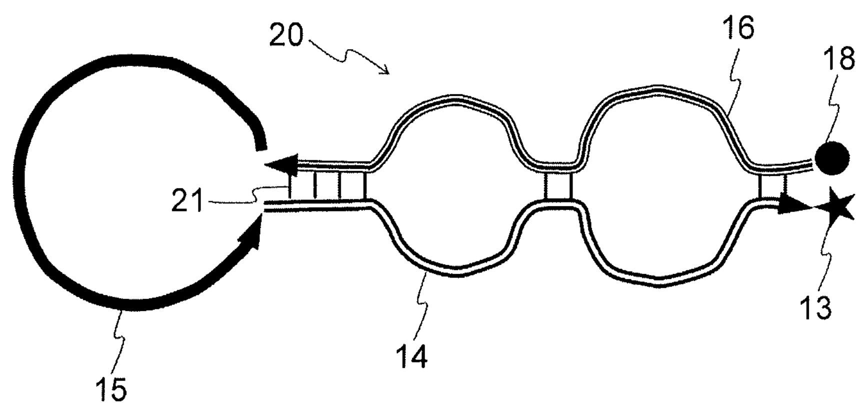
FIG. 2 is a self-hybridized structure of a self-amplifying folded oligonucleotide of FIG. 1.

Referring now to FIG. 2, there is shown a self-hybridized structure 20 of the linear structure of a self-amplifying folded oligonucleotide 10 where the stem-one oligonucleotide sequence 14 and the stem-two oligonucleotide sequence 16 made a stem structure through hydrogen bonds 21. The stem structure brings the signaling molecule 12 close to the signal modifying molecule 18 so that the signaling molecule 12 changes its state to the modified signaling molecule 13. For example, when the signaling molecule 12 and the signal modifying molecule 18 are fluorophore and quencher, the stem structure results in fluorescence quenching.

In further detail, still referring to FIG. 2, the stem-one oligonucleotide sequence 14 and stem-two oligonucleotide sequence 16 may have non-complement regions to each other, and therefore, the resulting stem structure may have one or more unhybridized region(s) as shown in FIG. 2.

Figure 3:
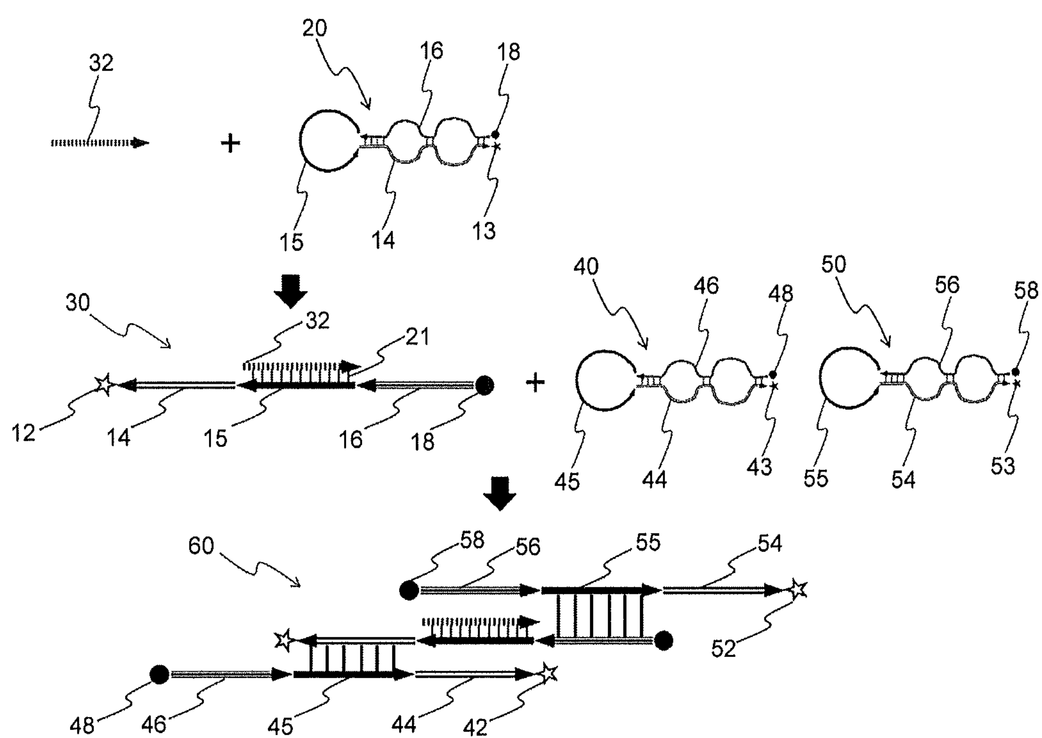
FIG. 3 is self-amplifying procedure of a self-amplifying folded oligonucleotide of the present invention.

Referring now to FIG. 3, there is shown an exponential signal amplifying procedure of the self-hybridized structures 20 by sensing a target oligonucleotide sequence 32. The self-hybridized structure 20 has a sensing oligonucleotide sequence 15 that is specific to a target oligonucleotide 32. When the target oligonucleotide 32 hybridizes to the sensing oligonucleotide sequence 15 of the self-hybridized structure 20, the resulting double strand oligonucleotide becomes rigid and unzips the stem structure 30. As a result, the modified signaling molecule 13 is placed apart from the signal modifying molecule 18 so that the modified signaling molecule 13 changes its state to the signaling molecule 12. For example, when the signaling molecule 12 and the signal modifying molecule 18 are fluorophore and fluorescence quencher, the signaling molecule 12 can generate fluorescence signal after the unzipping.

In further detail, still referring to FIG. 3, the unzipped stem-one oligonucleotide sequence 14 and stem-two oligonucleotide sequence 16 are now free to move, and therefore, the two stem oligonucleotide sequences 14, 16 can hybridize and unzip two other self-hybridized structures of linear structures of self-amplifying folded DNA (or RNA or PNA). The stem-one oligonucleotide sequence 14 is complement to a sensing oligonucleotide sequence 45 of self-hybridized structures 40 and the stem-two oligonucleotide sequence 16 is complement to a sensing oligonucleotide sequence 55 of self-hybridized structures 50. Therefore, the unzipped stem-one oligonucleotide sequence 14 and stem-two oligonucleotide sequence 16 are able to hybridize and unzip self-hybridized structures 40 and 50, respectively. As a result, four stem oligonucleotide sequences 44, 46, 54, 56 are now free to move, and therefore, modified signaling molecules 43 and 53 are placed apart from the signal modifying molecule 48 and 58 so that the modified signaling molecule 43, 53 change their states to the signaling molecule 42 and 52, respectively. For example, when the signaling molecule 42, 52 and the signal modifying molecule 48, 58 are fluorophore and fluorescence quencher, the signaling molecule 42, 52 can generate fluorescence signal after the unzipping.

In further detail, still referring to FIG. 3, the target oligonucleotide 32 hybridizes and unzip one self-hybridized structure 20, and then, results in one target oligonucleotide hybridized and unzipped structure 30, and therefore, results in one signaling molecule 12. In addition, the resulting target oligonucleotide hybridized and unzipped structure 30 now reveals two reaction sites, namely the stem-one oligonucleotide sequence 14 and stem-two oligonucleotide sequence 16. The stem-one oligonucleotide sequence 14 and stem-two oligonucleotide sequence 16 hybridize to and unzip each of the self-hybridized structure 40 and 50, and therefore, results in two signaling molecule 42 and 52. In addition, the resulting self-amplified target oligonucleotide hybridized and unzipped structure 60 reveals four reaction sites, namely the stem-one oligonucleotide sequence 44, 54 and stem-two oligonucleotide sequence 46, 56. This reaction increases exponentially, and therefore, single target oligonucleotide 32 results in exponentially increasing number of the signaling molecules, resulting in highly sensitive target oligonucleotide sensing.

Figure 4:
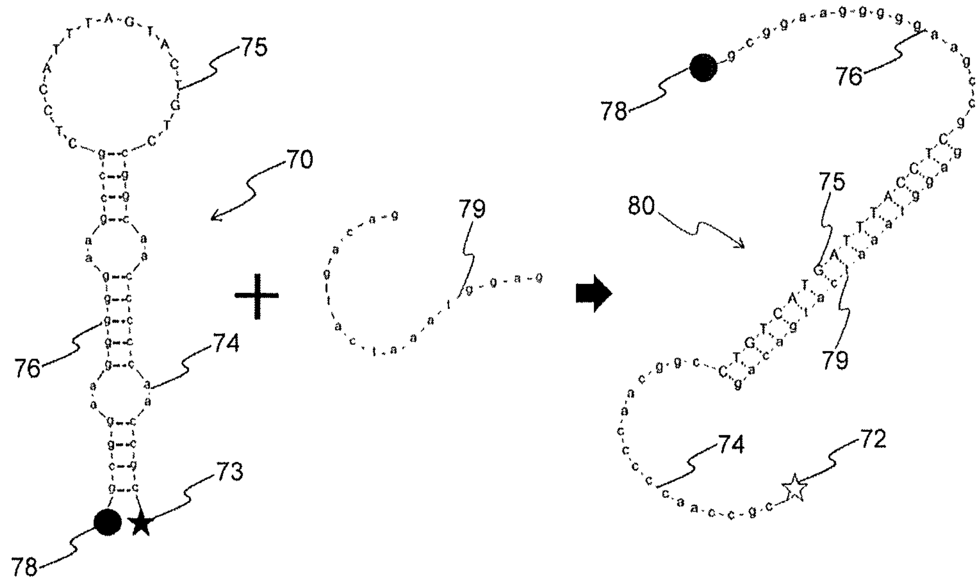
FIG. 4 is an example of HIV diagnosis with a self-amplifying sequence of a self-amplifying folded DNA (or RNA or PNA) (SEQ ID NOs.: 1 and 2)

Referring now to FIG. 4, there is shown an example of HIV diagnosis with a self-amplifying folded DNA. The self-amplifying folded DNA 70 includes a sensing oligonucleotide sequence (5'-CTCCATTTAGTACTGTC-3'; SEQ ID NO.: 5) 75 for sensing the target DNA sequence HIV 1 HXB2CG (5'-GACAGTACTAAATGGAG-3'; SEQ ID NO.: 2) 79, a stem-one DNA sequence (5'-cggcaaccccccaaccgc-3'; SEQ ID NO.: 6) 74, a stem-two DNA sequence (5'-gcggaagggg-gaagccg-3'; SEQ ID NO.: 7) 76, a fluorophore (Alexa Fluor® 532) 72, and a fluorescence quencher (Iowa Black® FQ) 78. The self-amplifying folded DNA structure is simulated using a commercial software OligoAnalyzer 3.1 (Integrated DNA Technologies, Inc.) under a condition of [oligo]=0.25 μM, [Na+]=50 mM, [Mg2+]=0 mM, [dNTPs]=0 mM, Temperature=25° C., resulting in the folded structure 70. From the simulation, ΔH and ΔS are calculated as −107.3 kcal mole−1 and −0.3199 kcal K−1 mole-1, respectively, and therefore, the total difference in free energy, AG, is calculated as −11.93 kcal mole−1 and the melting temperature is calculated as 62.3° C. where the stem structure is unzipped. When the self-amplifying folded DNA 70 makes a stem structure, the fluorophore (Alexa Fluor® 532) 72 is close to the fluorescence quencher (Iowa Black® FQ) 78, and therefore, the fluorophore (Alexa Fluor® 532) 72 changes its state to no-fluorescence molecule 73.

In further detail, still referring to FIG. 4, the hybridization between the self-amplifying folded DNA 70 and sensing the target DNA sequence HIV 1 HXB2CG (5'-GACAGTACTAAATGGAG-3'; SEQ ID NO.: 2) 79 is simulated using the OligoAnalyzer 3.1 under the same conditions, resulting in the unzipped structure 80 and ΔG of −26.23 kcal mole−1. Because the AG (−26.23 kcal mole−1) is lower than that of making a stem structure (ΔG=−11.93 kcal mole−1), the target DNA sequence HIV 1 HXB2CG (5'-GACAGTACTAAATGGAG-3'; SEQ ID NO.: 2) 79 is able to hybridize and unzip the self-amplifying folded DNA 70. Then, the no-fluorescence molecule 73 is apart from the fluorescence quencher (Iowa Black® FQ) 78 and changes its state back to the fluorophore (Alexa Fluor® 532) 72. In addition, the stem-one DNA sequence (5'-cggcaacccccaaccgc-3'; SEQ ID NO.: 6) 74 and the stem-two DNA sequence (5'-gcggaagggggaagccg-3'; SEQ ID NO.: 7) 76 are now free to move and are able to hybridize and unzip two other self-amplifying folded DNA structures. As a result, a single target DNA sequence HIV 1 HXB2CG (5'-GACAGTACTAAATGGAG-3'; SEQ ID NO.: 2) 79 are able to trigger the exponential signal amplification. The stem-one DNA sequence 74 and the stem-two DNA sequence 76 are not limited to the sequences in this example (5'-cggcaacccccaaccgc-3'; SEQ ID NO.: 6) and (5'-gcggaagggggaagccg-3'; SEQ ID NO.: 7). In addition, the stem structure length and the number and size of unhybridized regions are not limited to this example.

Figure 5:
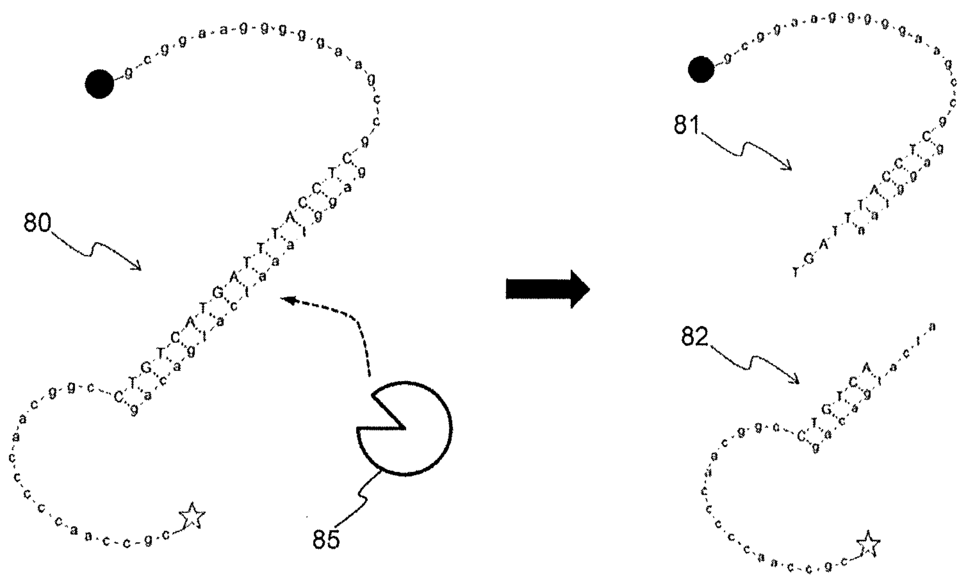
FIG. 5 illustrates restriction of a target oligonucleotide hybridized and unzipped structure of a 1 self-amplifying folded oligonucleotide (SEQ ID NOs.: 1, 3, and 4)

Referring now to FIG. 5, there is shown dividing procedure of a target oligonucleotide hybridized and unzipped structure of a self-amplifying folded oligonucleotide 80 for improving detection sensitivity. The target oligonucleotide hybridized and unzipped structure 80 is mixed with cutting molecule 85, resulting in dividing of the target oligonucleotide hybridized and unzipped structure 80 into two sub-molecules, namely unzipped-stem-one molecule 82 and unzipped-stem-two molecule 81. Then, the divided unzipped-stem-one molecule 82 and unzipped-stem-two molecule 81 higher degree of freedom compared to the target oligonucleotide hybridized and unzipped structure 80, and therefore, results in efficient hybridization and unzipping reactions.

In more detail, still referring to FIG. 5, example for the cutting molecule includes restriction enzyme.

Figure 6:
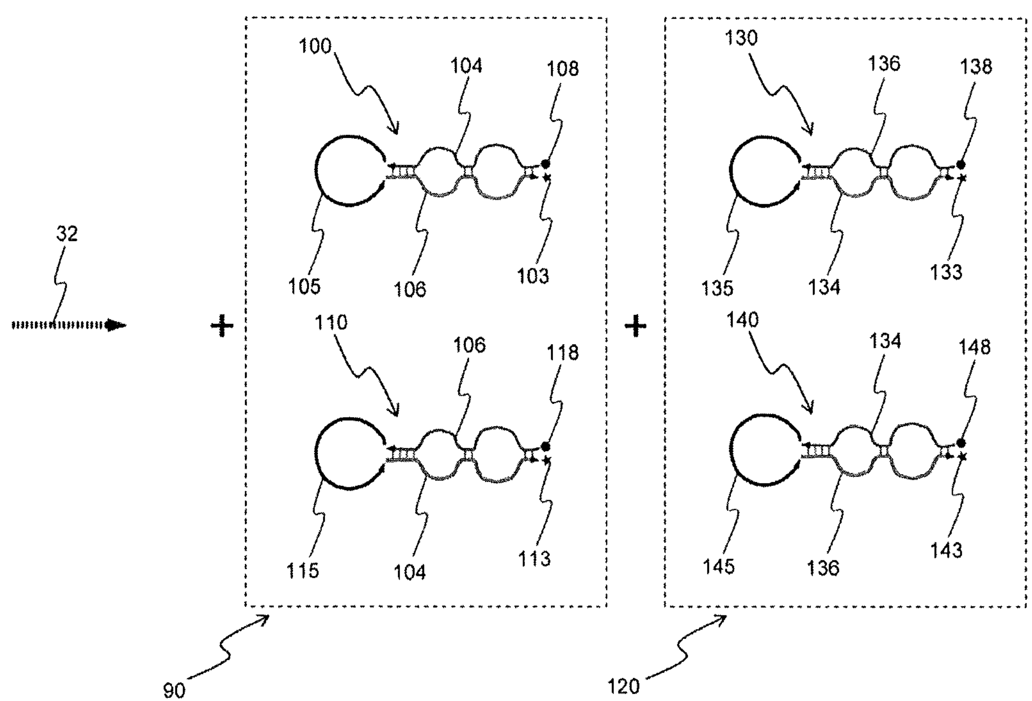
FIG. 6 is a self-amplifying folded oligonucleotide structure combination of the present invention.

Referring now to FIG. 6, there is shown a self-amplifying folded oligonucleotide combination for stable and efficient oligonucleotide sensing with low false-positive error. A target oligonucleotide 32 is mixed with two different self-hybridized structure sets 90 and 120. The self-hybridized structure set 90 has multiple copies of two different self-hybridized structures 100 and 110. The self-hybridized structure set 120 has multiple copies of two different self-hybridized structures 130 and 140. The self-hybridized structure 100 and 110 of the self-hybridized structure set 90 have two stem oligonucleotide sequences, namely a stem-one oligonucleotide sequence 104 and a stem-two oligonucleotide sequence 106, respectively. The stem-one oligonucleotide sequence 104 is complement to a sensing oligonucleotide sequence 135 of a self-hybridized structure 130, and therefore, is able to hybridize and unzip a self-hybridized structure 130 when the stem-one oligonucleotide sequence 104 is unzipped and free to move. The stem-two oligonucleotide sequence 106 is complement a sensing oligonucleotide sequence 145 of a self-hybridized structure 140, and therefore, is able to hybridize and unzip a self-hybridized structure 140 when the stem-two oligonucleotide sequence 106 is unzipped and free to move. The self-hybridized structure 130 and 140 of the self-hybridized structure set 120 have two stem oligonucleotide sequences, namely a stem-one oligonucleotide sequence 134 and a stem-two oligonucleotide sequence 136, respectively. The stem-one oligonucleotide sequence 134 is complement to a sensing oligonucleotide sequence 105 of a self-hybridized structure 100, and therefore, is able to hybridize and unzip a self-hybridized structure 100 when the stem-one oligonucleotide sequence 134 is unzipped and free to move. The stem-two oligonucleotide sequence 136 is complement a sensing oligonucleotide sequence 115 of a self-hybridized structure 110, and therefore, is able to hybridize and unzip a self-hybridized structure 110 when the stem-two oligonucleotide sequence 136 is unzipped and free to move.

In more detail, still referring to FIG. 6, the sensing oligonucleotide sequence 105 of the self-hybridized structure 100 is complement to the target oligonucleotide 32. Therefore, when a single target oligonucleotide 32 hybridizes to the sensing oligonucleotide sequence 105 of a self-hybridized structure 100 and unzip the stem structure of the self-hybridized structure 100, then, the resulting unzipped and free to move stem-one oligonucleotide sequence 104 and stem-two oligonucleotide sequence 106 are now able to hybridize and unzip self-hybridized structures 130 and 140, respectively. As a result, two of stem-one oligonucleotide sequence 134 and two of stem-two oligonucleotide sequence 136 are now free to move, and therefore, able to hybridize and unzip four self-hybridized structures in the self-hybridized structure set 90. This reaction increases exponentially, and therefore, single target oligonucleotide 32 results in exponentially increasing number of the signaling molecules for highly sensitive oligonucleotide sensing.

In further detail, still referring to FIG. 6, the two stem oligonucleotide sequences of the self-hybridized structure set 90, namely the stem-one oligonucleotide sequence 104 and stem-two oligonucleotide sequence 106 are designed to complement to sensing oligonucleotide sequences of the other self-hybridized structure set 120. In addition, the two stem oligonucleotide sequences of the self-hybridized structure set 120, namely the stem-one oligonucleotide sequence 134 and stem-two oligonucleotide sequence 136 are designed to complement to sensing oligonucleotide sequences of the other self-hybridized structure set 90. Therefore, each stem oligonucleotide sequence can be designed not to self-hybridize to its own sensing oligonucleotide sequences, resulting in stable formation of the stem structure. In addition, by storing the self-hybridized structure sets 90 and 120 separately, false-positive reaction triggering can be prevented. Then, the target oligonucleotide 32 can be sensed by mixing the target oligonucleotide 32 with the self-hybridized structure sets 90 and 120 together.

The advantages of the present invention include, without limitation, that it can exponentially amplify the signal output of a target oligonucleotide sensing without polymerase chain reaction (PCR). Therefore, the detection sensitivity is very high. The reaction and signal detection is very simple, and therefore, this technique can be applied for a point-of-care HIV diagnosis in resource-limited settings.

In broad embodiment, the present invention can be applied for any oligonucleotide sensing.

Example 1

HIV Diagnosis with a Self-Amplifying Folded DNA

The self-amplifying folded DNA 70 included a sensing oligonucleotide sequence (5'-CTCCATTTAGTACTGTC-3'; SEQ ID NO.: 5) 75 for sensing the target DNA sequence HIV 1 HXB2CG (5'-GACAGTACTAAATGGAG-3'; SEQ ID NO.: 2) 79, a stem-one DNA sequence (5'-cggcaacccccaaccgc-3'; SEQ ID NO.: 6) 74, a stem-two DNA sequence (5'-gcggaagggggaagccg-3'; SEQ ID NO.: 7) 76, a fluorophore (Alexa Fluor® 532) 72, and a fluorescence quencher (Iowa Black® FQ) 78. The self-amplifying folded DNA structure was simulated using a commercial software OligoAnalyzer 3.1 (Integrated DNA Technologies, Inc.) under a condition of [oligo]=0.25 μM, [Na+]=50 mM, [Mg2+]=0 mM, [dNTPs]=0 mM, Temperature=25° C., resulting in the folded structure 70. From the simulation, ΔH and ΔS were calculated as −107.3 kcal mole−1 and −0.3199 kcal K−1 mole−1, respectively, and therefore, the total difference in free energy, ΔG, was calculated as −11.93 kcal mole−1 and the melting temperature was calculated as 62.3° C. where the stem structure was unzipped. When the self-amplifying folded DNA 70 made a stem structure, the fluorophore (Alexa Fluor® 532) 72 was close to the fluorescence quencher (Iowa Black® FQ) 78, and therefore, the fluorophore (Alexa Fluor® 532) 72 changes its state to no-fluorescence molecule 73.

What is claimed is:

1. A signal-amplifying folded oligonucleotide combination comprising at least a first and a second different signal-amplifying folded oligonucleotide sets, wherein the signal-amplifying folded oligonucleotide comprises:

(a) a target sensing sequence;

(b) a first stem sequence; and (c) a second stem sequence wherein the (a) target sensing sequence is capable of forming a loop structure and capable of binding to a target oligonucleotide sequence, any one of the (b) first stem sequence and the (c) second stem sequence is labeled with a signaling molecule and the other one is labeled with a signal modifying molecule which may modify a signal from the signaling molecule in a folded oligonucleotide, and the (b) first stem sequence and the (c) second stem sequence are partially complementary to each other, wherein the first signal-amplifying folded oligonucleotide set comprises at least a first and a second different signal-amplifying folded oligonucleotides of the first set, and the second signal-amplifying folded oligonucleotide set comprises at least a first and a second different signal-amplifying folded oligonucleotides of the second set, wherein each first stem sequence of the first and the second signal-amplifying folded oligonucleotides and of the first set include oligonucleotide sequence that is complementary to a target sensing sequence of the first signal-amplifying folded oligonucleotide of the second set, and each second stem sequence of the first and the second signal-amplifying folded oligonucleotides of the first set include oligonucleotide sequence that is complementary to a target sensing sequence of the second signal-amplifying folded oligonucleotide of the second set, wherein each first stem sequence of the first and the second signal-amplifying folded oligonucleotides of the second set include oligonucleotide sequence that is complementary to a target sensing sequence of the first signal-amplifying folded oligonucleotide of the first set, and each second stem sequence of the first and the second signal-amplifying folded oligonucleotides of the second set include oligonucleotide sequence that is complementary to a target sensing sequence of the second signal-amplifying folded oligonucleotide of the first set.

2. The signal-amplifying folded oligonucleotide combination according to claim 1, wherein the target oligonucleotide sequence is a DNA, RNA or PNA sequence.

3. The signal-amplifying folded oligonucleotide combination according to claim 2, wherein the DNA or RNA sequence is a part of an HIV DNA or RNA sequence.

4. The signal-amplifying folded oligonucleotide combination according to claim 1, wherein the target sensing sequence comprises a restriction enzyme recognition site.

5. The signal-amplifying folded oligonucleotide combination according to claim 1, wherein the signaling molecule and the signal modifying molecule are respectively selected from the group consisting of a fluorophore and a fluorescence quencher, a Raman label and a surface-enhanced Raman scattering (SERS) inducing metal nanoparticle, and a fluorescence resonance energy transfer (FRET) acceptor and donor.

6. The signal-amplifying folded oligonucleotide combination according to claim 1, wherein the oligonucleotide comprises SEQ ID NO: 1.

7. The signal-amplifying folded oligonucleotide combination according to claim 1, wherein the oligonucleotide comprises of SEQ ID NO: 5.

8. The signal-amplifying folded oligonucleotide combination according to claim 1, wherein the oligonucleotide comprises SEQ ID NO: 6.

9. The signal-amplifying folded oligonucleotide combination according to claim 1, wherein the oligonucleotide comprises SEQ ID NO: 7.

10. The signal-amplifying folded oligonucleotide combination according to claim 1, wherein the target sensing sequence binds an oligonucleotide comprising SEQ ID NO: 2.

11. The signal-amplifying folded oligonucleotide combination according to claim 1, further comprising a third different signal-amplifying folded oligonucleotide set.

* * * * *